United States Patent [19]

Fischer, Jr. et al.

[11] 4,168,381

[45] Sep. 18, 1979

[54] ENHANCEMENT OF ENANTIOSELECTIVITY BY IODIDE SALTS OF RH(I) COMPLEXES IN THE REDUCTION OF PROCHIRAL IMIDAZOLINONES

[75] Inventors: Robert G. Fischer, Jr., Fairfield; Arnold Zweig, Westport; Sivaraman Raghu, Norwalk, all of Conn.

[73] Assignee: American Cyanamid Company, Stamford, Conn.

[21] Appl. No.: 896,253

[22] Filed: Apr. 14, 1978

Related U.S. Application Data

[63] Continuation-in-part of Ser. No. 806,421, Jun. 14, 1977, abandoned.

[51] Int. Cl.$^2$ ............................................. C07D 233/32
[52] U.S. Cl. .................................. 548/320; 260/429 R; 548/154; 548/155
[58] Field of Search .......................................... 548/320

[56] References Cited

U.S. PATENT DOCUMENTS

| | | | |
|---|---|---|---|
| 2,441,935 | 5/1948 | Duschinsky | 548/320 |
| 3,949,000 | 4/1976 | Violet | 260/326.14 T |
| 4,087,611 | 5/1978 | Raghu et al. | 424/270 |

OTHER PUBLICATIONS

Kagan, *Pure and Applied Chem.*, vol. 43, pp. 401–420 (1976).
Horner et al., *Chem. Absts.*, 1972, vol. 77, col. 48585m.
Levi et al., *Chem. Absts.*, 1975, vol. 82, col. 170229s.
Tanaka et al., *Chem. Absts.*, 1975, vol. 83, col. 178460b.
Kagan et al., *J.A.C.S.*, 1972, vol. 94 (18), pp. 6429–6433.

*Primary Examiner*—Alan L. Rotman
*Assistant Examiner*—Natalia Harkaway
*Attorney, Agent, or Firm*—H. G. Jackson

[57] ABSTRACT

A method for the attainment of enhanced enantioselectivity in the reduction of 3-acyl derivatives of 1-(2-alkoxyethyl)-4-phenyl-imidazolin-2-ones to the optically active 3-acyl derivatives of 1-(2-alkoxyethyl)-4-phenyl-2-imidazolidones for use in the direct manufacture of levamisole, (−), 2, 3, 5, 6-tetrahydro-6-phenylimidazo-[2,1-b]-thiazole, useful as an anthelmintic has been discovered. The method involves the preferred use of iodide salts of Rh(I) complexes of optically active bis-tertiary phosphines to achieve maximum enantioselectivity. The methods for preparing the iodide salts are disclosed.

5 Claims, No Drawings

ENHANCEMENT OF ENANTIOSELECTIVITY BY IODIDE SALTS OF RH(I) COMPLEXES IN THE REDUCTION OF PROCHIRAL IMIDAZOLINONES

CROSS REFERENCE TO RELATED APPLICATIONS

This application is a continuation-in-part of our co-pending application, Ser. No. 806,421, filed June 14, 1977, now abandoned.

BACKGROUND OF THE INVENTION

This invention relates to the asymmetric reduction of 1,4-disubstituted-4-imidazolin-2-ones to 1,4-disubstituted imidazolidine-2-ones and conversion of the latter to levamisole.

A novel process for the catalytic asymmetric synthesis of levamisole through reduction of prochiral intermediates is disclosed in U.S. Pat. No. 4,087,611 (1978). Asymmetric reduction is attained through catalysis by homogeneous asymmetric rhodium complexes acting on prochiral 1,4-disubstituted-4-imidazolin-2-ones. The maximum enantioselectivity disclosed was 33% enantiomeric excess achieved with a catalyst system derived from (+) DIOP and [Rh(COD)Cl]$_2$ acting on 1-(2-methoxyethyl)-3-acetyl-4-phenyl-4-imidazolin-2-one. The reduced product was converted to levamisole with retention of chirality.

Reduction of various substituted prochiral olefins using homogeneous asymmetric complexes of rhodium (I) salts as catalysts is a field that has been extensively examined in recent years. A review of the state of this art by H. B. Kagan has recently appeared in Pure and Applied Chem., 43, 401 (1976) which is incorporated herein by reference. For specified prochiral substrates the degree of enantioselectivity achieved in reduction has been found to be strongly influenced by the choice of the asymmetric tertiary phosphine derivative employed as a ligand in the catalyst complex. Different prochiral substrates have been found to require different asymmetric catalyst ligands for maximum enantioselectivity in catalytic reduction.

Specifically the use of rhodium complexes of bistertiary phosphines as catalysts is disclosed as follows:

U.S. Pat. No. 3,949,000 discloses asymmetric diphosphines which, when reacted with a rhodium (I) halogen salt, produces a rhodium complex. The rhodium complex is then used as a catalyst for the hydrogenation of precursors of amino acids.

Canadian Pat. No. 977,373 discloses rhodium coordination complexes, containing phosphine and at least one halogen ion, wherein the optical activity of the complex resides in the phosphine ligand. These complexes are useful as catalysts in the asymmetric hydrogenation of α-amino acids.

ASYMMETRIC CATALYSIS BY CHIRAL RHODIUM COMPLEXES IN HYDROGENATION AND HYDROSILYLATION REACTIONS, H. B. Kagan, "Pure and Applied Chemistry," 43, p. 401 (1976) discloses asymmetric catalysis of optically active enamides and precursers of α-amino acids using a chiral diphosphine rhodium complex as a homogeneous catalyst.

All of the above references are incorporated herein by reference.

Also, U.S. Pat. No. 4,087,611 (1978) [application Ser. No. 739,923 filed Nov. 8, 1976 which is a Continuation-in-part of U.S. patent application Ser. No. 680,302, filed Apr. 26, 1976, now abandoned,] discloses a process of using a chiral rhodium diphosphine catalyst to directly manufacture an optically active levamisole. See, e.g., U.S. Pat. No. 4,087,611 [Application 739,923, page 9] columns 5, 6, 7 and 8.

The greater enantioselectivity that can be achieved through catalytic asymmetric reduction, the greater the yield of levamisole or other useful enantiomer obtained.

There has been no previous evidence that the selection of the anion of the rhodium (I) complex salt used for homogeneous asymmetric catalytic reduction can have a significant effect on the degree of enantioselectivity obtained in the reduced substrate. In fact, for other substrate systems found in the prior art, it has been noted that the degree of enantioselectivity is independent of the anion. See, Knowles, J.A.C.S., 99, 5946 (1977); Kagan, supra, page 411. Since rhodium complexes with different anions are readily prepared by known methods, see, e.g., I. Chatt and L. M. Vananzi, J. Chem. Soc. 4735(1957), improvements in enantioselectivity obtained by such modification could readily be made practical.

SUMMARY AND DESCRIPTION OF THE INVENTION

The discovery has now been made that the iodide anion in homogeneous asymmetric complexes of rhodium salts substantially affects the degree of enantioselectivity in their catalytic reduction of certain prochiral olefins. The invention discloses that iodide salts of several asymmetric bis-phosphine complexes of rhodium substantially increase the degree of enantioselectivity in reduction of the prochiral 3-acyl derivatives of 1-(2-alkoxyethyl)-4-phenylimidazolin-2-one to optically active 1-(2-alkoxyethyl)-4-phenyl-2-imidazolidones relative to the enantioselectivity achieved with the corresponding bromide and chloride salts. The increased enantioselectivity achieved with the iodide salts provides a higher yield of the desired enantiomeric precursor of levamisole and subsequently a substantial increase in the yield of levamisole itself.

The method for the preparation of optically active 3-acyl derivatives of 1-(2-alkoxyethyl-4-phenyl-2-imidazolidones from 3-acyl derivatives of 1-(2-alkoxyethyl)-4-phenylimidazolin-2-one is by hydrogenating at a suitable temperature and pressure, as more fully described in the Examples, in the presence of a solvent and catalyst. The improvement of this invention comprises hydrogenating in the presence of a Rh(I) complex of an optically active bis-tertiary phosphine containing an iodide anion.

In a preferred embodiment, the complex is a Rh(I) complex of an enantiomer of optically active DIOP, a ditertiary phosphine of the formula:

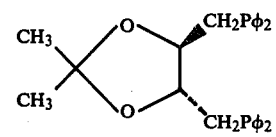

containing an iodide anion.

In a more preferred embodiment, the complex is a Rh(I) complex of an enantiomer of trans-bis(1,2-diphenylphosphinomethyl)cyclobutane containing an iodide anion. The preferred compound prepared by the use of this complex is an optically active acyl derivative of 1-(2-methoxyethyl)-4-phenyl-2-imidazolidone.

In a further preferred embodiment, the complex is a Rh(I) complex of a chiral enantiomer of N-butoxycarbonyl-4-diphenylphosphino-2-diphenylphosphinomethylpyrrolidine (BPPM) containing an iodide anion.

The invention also discloses that an effective iodide salt of the rhodium complex can be prepared by adding an excess of an alkali metal or other soluble iodide salt to a chloride salt of an asymmetric diphosphine complex of rhodium.

DETAILED DESCRIPTION OF THE INVENTION

EXAMPLE 1

1-(2-Methoxyethyl)-4-phenyl-4-imidazolin-2-one

Phenacyl bromide (60 g.), in 200 ml. of methylene chloride, is added over one hour to 2-methoxyethylamine (52 g.) in 100 ml. of methylene chloride, and cooled with an ice bath. The mixture is stirred for two hours at 0° C. Water (400 ml.) is added and the organic layer is separated, dried over anhydrous sodium sulfate and concentrated under aspirator vacuum (at room temperature). The viscous oil which remains (260 g.) is dissolved in methanol (200 ml.), cooled to 0° C. and acetic acid (80 ml.) and potassium cyanate (30 g.) is added. The mixture is refluxed for 90 minutes, the solvent removed under reduced pressure and the residue is taken up in 600 ml. of chloroform and washed with saturated sodium bicarbonate solution. The chloroform layer is washed, dried over sodium sulfate and concentrated to give a semisolid. Trituration with ether and filtration yields the title product as a yellow crystal; m.p. 152°–153° C.

EXAMPLE 2

1-(2-methoxyethyl)-4-phenyl-4-imidazolin-2-one

Phenacyl bromide (199 g.), in 400 ml. of chloroform is added over one half hour to a mixture of 2-methoxyethyl amine (82 g.) and triethylamine (152 g.) in 200 ml. of chloroform at 0° C. The mixture is stirred for two hours at 0°–10° C. Water (400 ml.) is added and the organic layer is separated and washed with another 400 ml. of water. The chloroform layer is cooled to 0° C. with an ice bath and glacial acetic acid (72 g.) potassium cyanate (89 g.) and methanol (100 ml.) are added. The mixture is refluxed for ninety minutes, cooled and washed with saturated sodium bicarbonate solution, and the organic layer is dried over anhydrous sodium sulfate and then concentrated to give a semisolid. Trituration with 300 ml of ether and filtration gives the title product as a yellow crystal; m.p. 152°–154° C.

EXAMPLE 3

1-(2-methoxyethyl)-3-acetyl-4-phenyl-4-imidazolin-2-one

Approximately 21.8 g of 1-(2-methoxyethyl)-4-phenyl-4-imidazolin-2-one and 120 ml. of acetic anhydride is refluxed together for four hours. The acetic anhydride is distilled out at reduced pressure. The residual semisolid is recrystallized from ethyl acetate to yield the title compound as a white solid; m.p. 81°–82° C.

EXAMPLE 4

Chiral Reduction of a 3-acetyl-imidazolin-2-one in Ethyl acetate using a catalyst derived from preformed [Rh(COD)I]$_2$ and (+) DIOP Into 15 ml of deoxygenated ethyl acetate is placed 1.0 g of 1-(2-methoxyethyl)-3-acetyl-4-phenylimidazolin-2-one, 30.5 mg of [Rh(COD)I]$_2$ and 45.2 mg of (+) DIOP. The (+) DIOP is prepared from (−) tartaric acid as described by H. G. Kagan and T. P. Deng in J. Amer. Chem. Soc., 94, 6429 (1972) incorporated herein by reference or is used as purchased from the Strem Chemical Co. Inc. of Beverly, Mass. The [Rh(COD)I]$_2$ is prepared by the method of Chatt and Venanzi, J. Chem. Soc., 4735 (1957), which is also incorporated herein by reference. COD is an abbreviation for 1,5-cyclooctadiene.

The solution is placed in an autoclave subjected to 1000 psig of hydrogen for 8 hours at 60° C. The ethyl acetate is removed under reduced pressure and the residue dissolved in 40 ml of diethylether and filtered. The filtrate is concentrated under reduced pressure to give a brown oil to which is added 45 ml of water and 5 g of sodium hydroxide. The mixture is refluxed for 1 hour, cooled and extracted with 2×50 ml of methylene chloride. The combined organic layer is dried over magnesium sulfate, filtered and the solvent removed at reduced pressure to give almost pure, optically active 1-(2-methoxyethyl)-4-phenyl-2-imidazolidine. An accurate measure of the degree of enantioselectivity is obtained by nuclear magnetic resonance (NMR) using the chiral shift reagent tris-[3-(trifluoromethylhydroxymethylene)-d-camphorato-]-europium III, Eu (tfc)$_3$. Use of this reagent shows the reduced material to contain 49% excess of the (+) enantiomer. The same reaction using [Rh(COD)Cl]$_2$ in place of [Rh(COD)I]$_2$ in the same molar proportion produces only 34% excess of the (+) enantiomer of the reduced material. Using [Rh(COD)Br]$_2$ in the same way produced a 36% excess of the (+) reduced material.

EXAMPLE 5

Chiral Reduction of a 3-Cyclohexoyl-imidazolin-2-one in Ethyl acetate using a catalyst derived from preformed [Rh(COD)I]$_2$ and (−) trans-bis (1,2-diphenylphosphinomethyl) cyclobutane Into 15 ml of deoxygenated ethyl acetate is placed 1.0 g of 1-(2-methoxyethyl)-3-cyclohexoyl-4 phenylimidazolin-2-one, 22.2 mg of [Rh(COD)I]$_2$ and 31.9 mg of (−) trans bis (1,2-diphenylphosphinomethyl)cyclobutane D$\alpha^{20}$ = −15.8) prepared by the method of U.S. Pat. No. 3,978,101, which is incorporated herein by reference. Hydrogenation and work-up are performed as in Example 4.

Analysis of the reduced product with the NMR shift reagent Eu(tfc)$_3$ shows the reduced material to contain a 57.5% excess of the (−) isomer. The same reaction using [Rh(COD)Cl]$_2$ in place of [Rh(COD)I]$_2$ in the same molar proportions produced only 23.4% excess of the (−) isomer.

EXAMPLE 6

Chiral Reduction of a 3-Acetyl-imidazolin-2-one in Ethyl Acetate using a catalyst derived from preformed [Rh(COD)I]₂ and (+) trans-bis(1,2-diphenylphosphinomethyl)cyclobutane The procedure of Example 5 is repeated with the same materials except that the (+) enantiomer was employed rather than the (−) enantiomer of trans-bis(1,2-diphenylphosphinomethyl)cyclobutane. The product enantiomer excess for both the [Rh(COD)I]₂ and the [Rh(COD)Cl]₂ was about the same as in Example 5 except that the (+) isomer of the product was obtained in excess.

EXAMPLE 7

Chiral reduction of a 3-Acetyl-imidazolin-2-one in ethyl acetate using a homogeneous rhodium catalyst as an iodide salt formed in situ containing the asymmetric bis phosphine (+) DIOP Into 15 ml of deoxygenated ethyl acetate is placed 1.0 g of 1-(2-methoxyethyl)-3-acetyl-4-phenylimidazolin-2-one, 19.1 ml of [Rh(COD)Cl]₂, 44.1 mg of (+) DIOP, and 23 mg of sodium iodide. The solution is hydrogenated and worked up as in Example I. Analysis by the NMR method of Example 4 showed the reduced material to contain a 49% excess of the (+) enantiomer. When the reaction is run in the absence of sodium iodide only a 34% excess of the (+) enantiomer of the reduced material is obtained.

EXAMPLE 8

Chiral Reduction of a 3-Benzoyl-imidazolin-2-one

Approximately 1.5 g of 1-(2-methoxyethyl)-3-benzoyl-4-phenylimidazolin-2-one, 32.9 mg of [Rh(COD)I]₂ and 64.5 mg of (+) DIOP are dissolved under nitrogen in 23 ml of deoxygenated ethyl acetate. The solution is hydrogenated and the product obtained as in Example 4. The product contains a 24 percent excess of one enantiomer. The same reaction with [Rh(COD)Cl]₂ gives an 11 percent excess of one enantiomer.

EXAMPLE 9

Chiral Reduction of a 3-(p-trifluoromethylbenzoyl)imidazolin-2-one

Approximately 1.5 g of 1-(2-methoxyethyl)-3-(p-trifluoromethylbenzoyl)-4-phenylimidazolin-2-one, 32.0 mg of [Rh(COD)I]₂, and 66.1 mg of (+) DIOP are dissolved under nitrogen in 23 ml of deoxygenated ethyl acetate. The solution is hydrogenated and the product obtained as in Example 4. The product contains a 34 percent excess of one enantiomer. The same reaction with [Rh(COD)Cl]₂ gives a 24 percent excess of one enantiomer.

EXAMPLE 10

Chiral Reduction of a 3-(o-methoxybenzoyl)imidazolin-2-one

Approximately 1.5 g of 1-(2-methoxyethyl)-3-(o)-methoxybenzoyl)-4-phenylimidazolin-2-one, 34.1 mg of [Rh(COD)I]₂ and 67.1 mg of (+) DIOP are dissolved under nitrogen in 23 ml of deoxygenated ethyl acetate. The solution is hydrogenated and the product obtained as in Example 4. The product contains a 37 percent excess of one enantiomer. The same reaction with [Rh(COD)]₂ gives a 20 percent excess of one enantiomer.

EXAMPLE 11

Chiral Reduction of a 3-acetyl-imidazolin-2-one in ethyl acetate using a catalyst derived from performed [Rh(COD)I]₂ and (−) CBDP Using the procedure and quantities of solvent and imidazolin-2-one of Example 4, hydrogenation was performed with a catalyst derived from 26.7 mg of [Rh(COD)I]₂ and 39.0 mg of (−) trans bis (1,2-diphenylphosphinomethyl)cyclobutane, the latter as described in Example 5. Hydrogenation was performed as in Example 4 except that an initial pressure of 500 psig was employed and the hydrogenation was allowed to proceed for 24 hour work-up as in Example 4 gave complete reduction and produced a 55% excess of the (−) isomer of the reduced product. When the reaction was performed under identical conditions except using 24.3 mg of [Rh(COD)Br]₂ in place of the iodide, the excess of the (−) isomer obtained was only 31.6%.

EXAMPLE 12

Chiral Reduction of a 3-acetyl-imidazolin-2-one in various solvents using a catalyst derived from preformed [Rh(COD)I]₂ and (−) CBDP Using the procedure and imidazolin-2-one substrate of Example 4, hydrogenations were performed with a catalyst derived from [Rh(COD)I]₂ and (−) trans-bis-(1,2-diphenylphosphinomethyl)cyclobutane (described in Example 5) in 1:2.2 molar proportions. In acetone after 8 hours under 1000 psig H₂ at 60° C., a 63% excess of the (−) isomer of the reduced material was obtained. In tert-butyl acetate after 24 hours under 500 psig H₂ at 60°C. a 61.3% excess of the (−) isomer of the reduced material was obtained. In ethyl propionate these conditions gave 57.5% excess, and in methyl acetate a 58.1% excess was obtained. Reduction performed in methyl ethyl ketone, diethyl ketone, cyclohexanone and methyl isobutyl ketone under similar conditions gave 58.7%, 57.5%, 43.9% and 48.1% excess of the (−) isomer of the reduced material, respectively. Reduction in acetone at 60° and 500 psig H₂ gave a 61.3% excess and in 2-methyl-1-butyl acetate these conditions gave a 60% excess of the (−) isomer of the reduced material.

EXAMPLE 13

Chiral Reduction of a 3-acetyl-imidazolin-2-one using a catalyst derived from preformed [Rh(CCD)I]₂ and BPPM Using the procedure and imidazolin-2-one substrate of Example 4, hydrogenations were performed with a catalyst derived from [Rh(COD)I]₂ and (2S,4S)-N-butoxycarbonyl-4-diphenylphosphino-2-diphenylphosphinomethylpyrrolidine (BPPM) (described in an article by K. Achiwa in J. Amer. Chem. Soc., 98, 8265 (1976)]in 1:2.2 molar proportions. In ethyl acetate after 20 hours under 1000 psig H₂ at 60° C., a 61.3% excess of the (−) isomer of the reduced material was obtained. The (2R,4R) isomer of BPPM provided the same excess of the (+) isomer of the reduced material.

EXAMPLE 14

Chiral Reduction of a 3-acetyl-imidazolin-2-one using a catalyst derived from preformed [Rh(COD)Cl]$_2$ and BPPM Using the procedure and imidazolin-2-one substrate of Example 4, hydrogenations were performed with a catalyst derived from [Rh(COD)Cl]$_2$ and (2S,4S)-N-butoxycarbonyl-4-diphenylphosphino-2-diphenylphosphinomethylpyrolidine (BPPM) (described in an article by K. Achiwa in J. Amer. Cham. Soc., 98, 8265 (1976)) in 1:2.2 molar proportions. In ethyl acetate after 22 hours under 1000 psig H$_2$ at 60° C., a 24.6% excess of the (−) isomer of the reduced material was obtained. The (2R,4R) isomer of BPPM) provided the same excess of the (+) isomer of the reduced material.

We claim:

1. In a method for the preparation of optically active 3-acyl derivatives of 1-(2-alkoxyethyl-4-phenyl-2-imidazolidones from 3-acyl derivatives of 1-(2-alkoxyethyl)-4-phenylimidazolin-2-one by hydrogenating at a suitable temperature and pressure in the presence of a solvent and catalyst, the improvement comprising: hydrogenating in the presence of a Rh(I) complex of optically active bis-tertiary phosphine containing an iodide anion.

2. The method according to claim 1, wherein said complex is a Rh(I) complex of an enantiomer of trans-bis(1,2-diphenylphosphinomethyl)cyclobutane containing an iodide anion.

3. The method according to claim 1, wherein said complex is a Rh(I) complex of an enantiomer of optically active DIOP, a ditertiary phosphine of the formula:

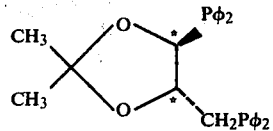

containing an iodide anion.

4. The method according to claim 1, wherein said complex is a Rh(I) complex of a chiral enantiomer of N-butoxycarbonyl-4-diphenylphosphino-2-diphenylphosphinomethylpyrrolidine (BPPM) containing an iodide anion.

5. The method according to claim 1, wherein the compound prepared is an optically active acyl derivative of 1-(2-methoxyethyl)-4-phenyl-2-imidazolidone.

* * * * *